United States Patent [19]

Krueger et al.

[11] 4,139,554
[45] Feb. 13, 1979

[54] PROCESS OF PRODUCING N,N-DIMETHYLAMINO METHANE DIPHOSPHONIC ACID

[75] Inventors: Friedrich Krueger, Edingen; Walter Michel, Ilvesheim, both of Fed. Rep. of Germany

[73] Assignee: Joh. A. Benckiser GmbH, Ludwigshafen, Fed. Rep. of Germany

[21] Appl. No.: 896,154

[22] Filed: Apr. 13, 1978

[30] Foreign Application Priority Data

May 18, 1977 [DE] Fed. Rep. of Germany ....... 2722539

[51] Int. Cl.$^2$ ............................................. C07F 9/38
[52] U.S. Cl. ................................................ 260/502.5
[58] Field of Search ................................... 260/502.5

[56] References Cited

U.S. PATENT DOCUMENTS

| 3,846,420 | 11/1974 | Wollmann et al. | 260/502.5 |
| 3,870,750 | 3/1975 | Walmann et al. | 260/502.5 |
| 4,006,182 | 2/1977 | Ploger et al. | 260/502.5 |

FOREIGN PATENT DOCUMENTS

| 1,958,123 | 5/1971 | Fed. Rep. of Germany | 260/502.5 |
| 5,095,227 | 7/1975 | Japan | 260/502.5 |

*Primary Examiner*—Joseph E. Evans
*Attorney, Agent, or Firm*—Richard L. Schwaab

[57] ABSTRACT

N,N-Dimethylaminomethane diphosphonic acid is produced in an advantageous, simple, and economical manner and in a high yield by reacting dimethylformamide, phosphorous acid, and phosporus oxychloride.

4 Claims, No Drawings

PROCESS OF PRODUCING N,N-DIMETHYLAMINO METHANE DIPHOSPHONIC ACID

BACKGROUND OF THE INVENTION

1. Field of the Invention

The present invention relates to a simple and advantageous process of producing N,N-dimethylamino methane diphosphonic acid. Said acid is distinguished from the known amino alkane diphosphonic acid by its superior properties, more particularly its superior inhibitory effect on scale and deposit formation in aqueous systems and its anticorrosive activity. For this reason it has proved to be useful for many purposes.

2. Description of the Prior Art

A number of processes to produce amino alkane diphosphonic acids are known. Amino alkane diphosphonic acids are obtained according to German Offenlegungsschrift No. 1,958,123 by reacting monocarboxylic acid amide with phosphorus trihalogenides and subsequently hydrolyzing the resulting reaction product. Working with phosphorus halogenides especially with phosphorus trichloride, however, has a number of disadvantages.

It is known, for instance, that phosphorus trichloride reacts with small amounts of water such as they are encountered as traces of moisture in any apparatus which has not been dried thoroughly, and forms yellow, insoluble decomposition products. These impurities are causing considerable trouble especially when the phosphonic acid is precipitated in crystalline form in the reaction vessel already during the reaction. It is then necessary to again dissolve the precipitated phosphonic acid in order to separate the impurities. It is also well known to an expert that when carrying out the reaction on a semi-technical scale, there are formed frequently not only such insoluble decomposition products but also monomeric phosphine. Phosphine, however, is highly toxic and has a tendency to self-ignition. Therefore, specific precautionary measures must be taken when producing amino alkane diphosphonic acids according to the aforesaid process.

According to German published application No. 2,048,912 carboxylic acid amide dichlorides or dibromides are reacted with phosphorous acid whereby amino alkane diphosphonic acids are obtained. This process, however, is quite complicated because it requires additional process steps in order to produce the starting materials, the carboxylic acid amide dihalogenides.

SUMMARY OF THE INVENTION

It is one object of the present invention to provide a novel, highly advantageous, and simple process of producing the N,N-dimethylamino methane diphosphonic acid, which process does not have the above mentioned disadvantages.

Other objects of the present invention and advantageous features thereof will become apparent as the description proceeds.

In principle the process according to the present invention is characterized by the reaction of N,N-dimethylformamide with phosphorous acid and phosphorus oxychloride.

Preferably this reaction is carried out by first charging the reaction vessel with a mixture of N,N-dimethylformamide and phosphorous acid and then adding phosphorus oxychloride thereto. The temperature of the reaction solution increases during dropwise addition of phosphorus oxychloride and hydrogen chloride gas escapes. It is not necessary to cool the reaction mixture. As soon as dropwise addition of the phosphorus oxychloride is completed, the reaction mixture is diluted with water. The N,N-dimethylamino methane diphosphonic acid crystallizes as a pure, white compound from the aqueous reaction solution in a high yield exceeding 80%. On concentrating the mother liquor by evaporation and adding, if necessary, thereto a precipitating agent, such as a water soluble solvent, for instance, acetone, methanol, or ethanol, it is possible to isolate further amounts of said phosphonic acid. It is also possible to use the mother liquor directly as additive to prevent scale formation in aqueous systems. Thus it is not necessary to isolate the residual phosphonic acid from the mother liquor. Insoluble decomposition products, as they are obtained on using phosphorus trichloride, are not produced with phosphorus oxychloride.

It has proved to be of advantage to react the N,N-dimethylformamide with phosphorous acid and phosphorus oxychloride in the molar proportion of 1 : 1.0–1.5 : 0.3–0.5.

The process according to the present invention has not only the advantage that the yield is much higher than when producing the phosphonic acid in accordance with known processes, but the process can also be carried out in a considerably simpler manner since a very considerable portion of the resulting phosphonic acid crystallizes directly from the reaction mixture and need not be precipitated by the addition of an organic solvent as this is necessary when proceeding according to the known processes. A further very important advantage of the claimed process is the fact that the reaction proceeds without having to supply energy and that no reflux cooler and thus cooling water are required. As a result thereof the process is highly economical and the production costs are low.

DESCRIPTION OF THE PREFERRED EMBODIMENT

The following example serves to illustrate the present invention without, however, being limited thereto.

EXAMPLE 146.2 g. (2 moles) of N,N-dimethylformamide and 164 g. (2 moles) of phosphorous acid are charged into the reaction vessel. The mixture is stirred vigorously. 115 g. (0.75 moles) of phosphorus oxychloride are added drop by drop to said mixture within about 10 minutes. During said dropwise addition the temperature increases gradually to a temperature of 120° to 130° C. and hydrogen chloride gas is continuously developed. After addition of the phosphorus oxychloride 200 cc. of cold water are added to the reaction mixture. The phosphonic acid precipitates from the solution which initially is clear as water, within a few minutes. The cooled crystalline sludge is filtered off by suction and is dried. 177.4 g. of pure, white N,N-dimethylamino methane diphosphonic acid are obtained as a crystalline product. The yield is 81.0% of the theoretical yield calculated for phosphorous acid.

As is evident, the reaction mixture is neither cooled, nor heated during the reaction. Reflux cooling is also not necessary.

About 15 g. of the phosphonic acid can be isolated from the mother liquor by concentration and addition of ethanol, methanol, or acetone.

Analysis: Calculated: N = 6.4%; P = 28.3%; Found: N = 6.4%; P = 28.9%.
The resulting phosphonic acid has proved to be identical with the N,N-dimethylamino methane diphosphonic acid produced according to German published application No. 1,958,123 as can be demonstrated by its infrared spectrum.

Of course, many changes and variations in the proportions of the reactants, in the manner in which the reaction product is recovered from the reaction mixture, and the like can be made by those skilled in the art in accordance with the principles set forth herein and in the claims annexed hereto.

We claim:
1. In a process of producing N,N-dimethylamino methane diphosphonic acid, the steps comprising reacting N,N-dimethylformamide with phosphorous acid and phosphorus oxychloride and allowing the resulting N,N-dimethylamino methane diphosphonic acid to crystallize from the reaction mixture.

2. The process of claim 1, in which N,N-dimethylformamide, phosphorous acid, and phosphorus axychloride are reacted in the molar proportion of 1 : 1.0–1.5 :0.3–0.5.

3. The process of claim 1, in which the phosphorus oxychloride is added drop by drop to the mixture of N,N-dimethylformamide and phosphorous acid and water is added to the reaction mixture to cause crystallization of N,N-dimethylamino methane diphosphonic acid.

4. The process of claim 3, in which a water soluble solvent is added to the mother liquor remaining after separation of the crystallized N,N-dimethylamino methane diphosphonic acid, so as to precipitate further amounts of the phosphonic acid.

* * * * *